United States Patent [19]

Schwarz et al.

[11] Patent Number: 5,721,258
[45] Date of Patent: Feb. 24, 1998

[54] PRIMARY AND SECONDARY NEUROPROTECTIVE EFFECT OF FLUPIRTINE IN NEURODEGENERATIVE DISEASES

[75] Inventors: Michael Schwarz, Essen; Gabriela Pergande, Offenbach; Jürgen Engel, Alzenau; Bernd Nickel, Mühltal; Heinz Ulrich, Niedernberg; Stefan Szelenyi, Schwaig, all of Germany

[73] Assignee: Asta Medica Aktiengesellschaft, Dresden, Germany

[21] Appl. No.: 602,742

[22] PCT Filed: Aug. 10, 1994

[86] PCT No.: PCT/EP94/02649

§ 371 Date: Apr. 19, 1996

§ 102(e) Date: Apr. 19, 1996

[87] PCT Pub. No.: WO95/05175

PCT Pub. Date: Feb. 23, 1995

[30] Foreign Application Priority Data

Aug. 17, 1993 [DE] Germany .................. 4327516.8

[51] Int. Cl.[6] .................................................. A61K 31/44
[52] U.S. Cl. ........................................................ 514/352
[58] Field of Search ............................................ 514/352

[56] References Cited

U.S. PATENT DOCUMENTS 5,162,346  11/1992  Lobisch et al. ................. 514/356

FOREIGN PATENT DOCUMENTS

| 199 951 | 12/1986 | European Pat. Off. . |
| 467 164 | 1/1992 | European Pat. Off. . |
| 33 37 593 | 5/1984 | Germany . |
| 2 084 138 | 4/1982 | United Kingdom . |

OTHER PUBLICATIONS

Schwarz et al: "N–Methyl–D–Aspartate (NMDA)–Mediated Muscle Relaxant Action of Flupirtine in Rat", Neuroreport, vol. 5, No. 15, Oct. 1994, pp. 1981–1984.

Friedel, et al: "Flupirtine", Drugs, vol. 45, NO. 4, Apr. 1993, pp. 548–569.

Seaman, et al: "Flupirtine", Curr. Probl. Epilepsy, vol. 4, 1986, pp. 135–145.

Sheridan, et al: "Pilot Stody of Flupirtine in Refractory Seizures," Neurology, vol. 36, 1986, p. 85.

*Primary Examiner*—William R. A. Jarvis
*Attorney, Agent, or Firm*—Cushman Darby & Cushman IP Group of Pillsbury Madison & Sutro LLP

[57] ABSTRACT

The NMDA-antagonistic effect of flupirtine permits the preparation of medicaments for the treatment of cerebral ischemia, neurodegenerative disorders, traumatic brain and bone marrow damage, and other illnesses.

15 Claims, 9 Drawing Sheets

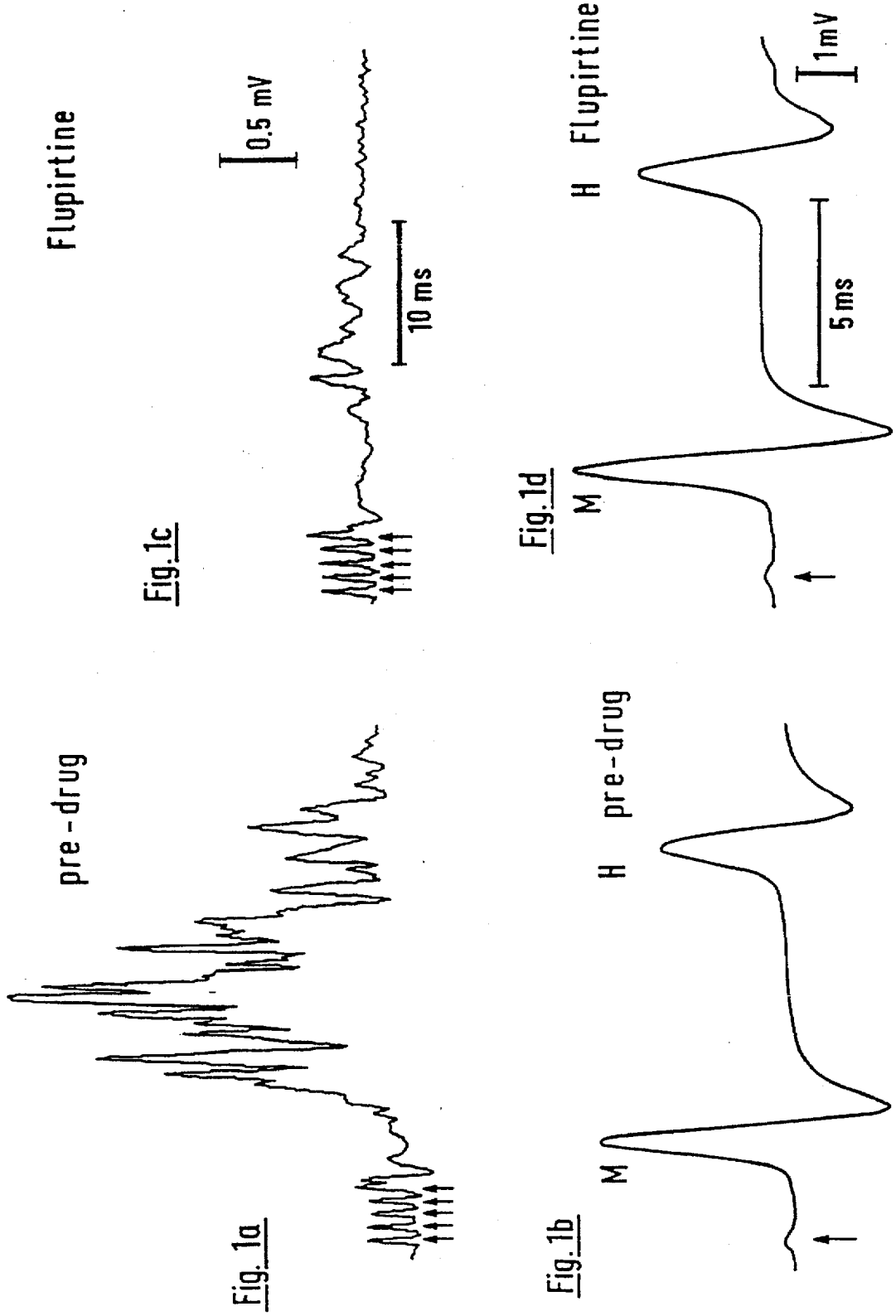

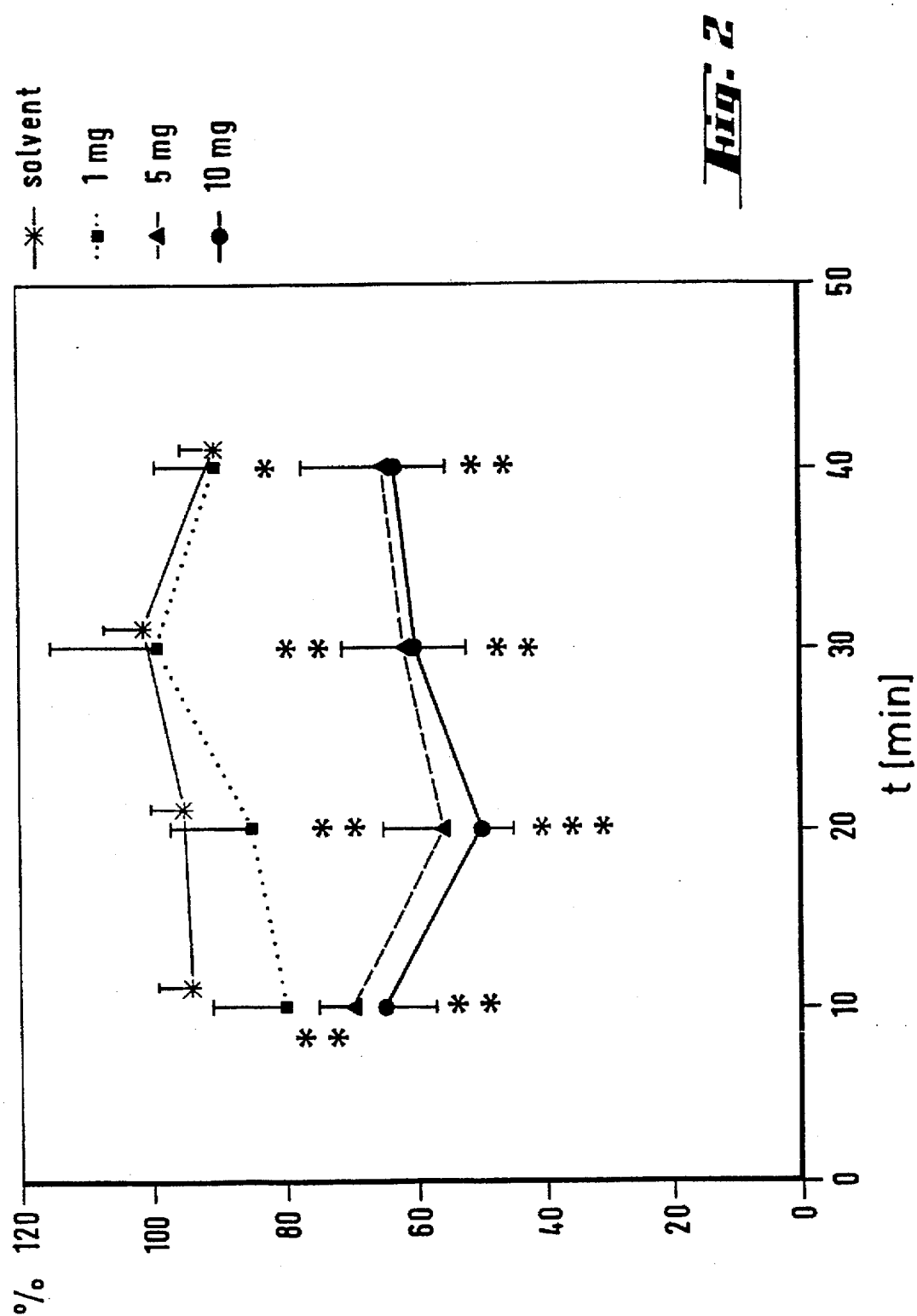

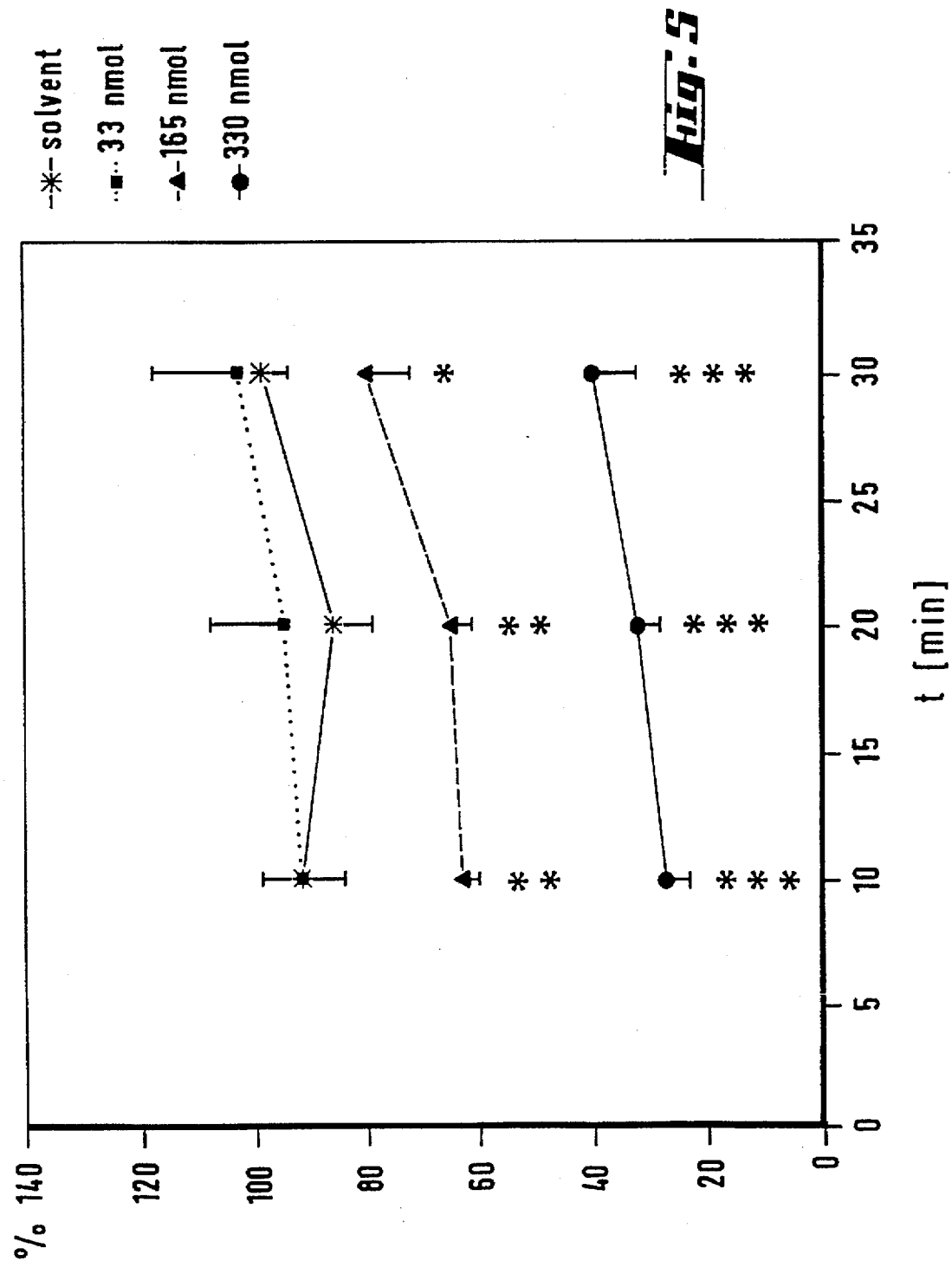

PRIMARY AND SECONDARY NEUROPROTECTIVE EFFECT OF FLUPIRTINE IN NEURODEGENERATIVE DISEASES

This application claims benefit of international application PCT/EP94/02649, filed Aug. 10, 1994.

BACKGROUND OF THE INVENTION

FIELD OF THE INVENTION

The invention relates to the use of flupirtine in medicaments for the treatment of cerebral ischemia, neurodegenerative disorders, traumatic brain and bone marrow damage, epileptic attacks and other illnesses.

BACKGROUND INFORMATION

Flupirtine (Katadolon®) is a new, centrally acting, non-opiate analgesic. (Jakovlev, V. Sofia, R. D., Achterrath-Tuckermann, U., von Schlichtegroll, A., Thiemer, K., Arzneim.-Forsch./Drug Res. 35 (I), 30 (1985); Nickel, B., Herz, A., Jakovlev, V., Tibes, U., Arzneim.-Forsch/Drug Res. 35 (II), 1402 (1985). Flupirtine develops its central analgesic effects via mechanisms of action that differ from those of the opiate/opioid analgesics. (Nickel, B., Postgrad. med. J. 63 (Suppl. 3), 19 (1987); Szelenyi, I., Nickel, B., Borbe, H. O., Brune K., Br. J. Pharmacol. 143, 89 (1989)). Electrophysiological investigations have shown that flupirtine is able to intervene in the nociceptive process both at the supraspinal and at the spinal level. (Carlsson, K. H. Jurna, I., Eur. J. pharmacol. 143, 89 (1987); Bleyer, H., Carlsson K. H., Erkel H. J., Jurna, I., Eur. J. Pharmacol 151, 259 (1988); Nikel, B. Aledter, A., Postgrad Med. J. 63 (Suppl. 3) 41 (1987)).

Flupirtine has hitherto been used in the treatment of acute states of pain caused by diseases of the locomotor apparatus. Flupirtine has also been successfully used in patients with nerve pains, cancer pain, vasomotor and migraine headaches, post-operative pain, after injuries, burns, erosions, in dysmenorrhea and toothache. These indications and the dosages to be used are given in the professional information (Katadolon®, monoanalgesic, scientific leaflet, second revised edition April 1992, published by ASTA Medica AG). Combination medicaments of flupirtine with non-steroidal anti-inflammatory agents are described in EP 189 788. In these indications it is of advantage that flupirtine has not only analgesic, but also a muscle-relaxant properties, as described in German published specification 41 22 166 4.

Chemically speaking, flupirtine is the maleate of 2-amino-3-ethyl-ethoxycarbonylamino-6[5-fluorobenzyl]-aminopyridine. The synthesis of flupirtine and its pharmaceutically acceptable salts is described in EP 160 865 and 199 951. Flupirtine maleate has a chemical structure that cannot be assigned to hitherto known analgesically acting pharmaceuticals. Flupirtine is a colourless, crystalline, almost odourless powder with slightly bitter-sweet taste. It is only moderately soluble in water. The analgesic effect of flupirtine has been demonstrated in various animal experiments on pain models after mechanical (Haffner test), thermic (hotplate test), electrical (electropain test, dental pulp irritation), chemical (writhing test) and chemical-mechanical irritation (Randall-Selito test) in mouse, rat and dog. More information on the effect and side effects of the monoanalgesic flupirtine are given in the scientific leaflet (Katadolon®, monoanalgesic, scientific leaflet, second revised edition April 1992, published by ASTA Medica AG).

Pharmacological examinations show that flupirtine has both a spinal and a supraspinal point of attack. Blockade experiments with antagonists have shown that neither the serotoninergic nor the opioid system can be involved in mediating the antinociceptic effect of flupirtine. The most probable explanation for the flupirtine-induced analgesia is the involvement of descending noradrenergic pain-modulating paths (I. Szelenyi, B. Nickel, H. O. Borbe, K. Brune Br. J. Pharmacol. (1989), 97, 835–842), although flupirtine has no binding affinity for $\alpha_1$- or $\alpha_2$-adrenergic receptors (B. Nickel et al., Br. J. Pharmacol. (1989) 97, 835).

In addition, the absence of affinity for the opiate receptors of rat brain also speaks against an opiate-like mechanism of action of flupirtine. According to these results, a mechanism of action of flupirtine corresponding to the opiates can be excluded. Tolerance and dependence have not been observed either.

SUMMARY OF THE INVENTION

When investigating the muscle-relaxant effect of flupirtine in the rat it has now surprisingly been found that the effect of flupirtine can be inhibited by the excitatory amino acid N-methyl-D-aspartate (NMDA). These findings suggest that the effect of flupirtine is at least in part mediated by inhibition of NMDA-mediated stimulation. This opens up the possibility of using flupirtine as an antagonist of excitatory amino acids to treat illnesses that are mediated by excitatory amino acids, such as cerebral ischemia, neurodegenerative diseases and epileptic attacks.

DETAILED DESCRIPTION OF THE INVENTION

Description of the Experiments:

The in vivo experiments were carried out in rats. Male Wistar rats (body weight 250–280 g) were anesthesised with urethane (400 mg/kg i.p.) and a-choralose (80 mg/kg i.p.). The Nervus tibialis was stimulated with transcutaneous needle electrodes to the lead of the H-reflex (individual square impulses of 0.2 ms duration with a stimulus strength twice that of the reflex threshold). EMG leads were recorded from the plantar foot muscles using a pair of cutaneous Klippel electrodes.

Electrical stimulation of the Nervus Tibialis with low stimulus strengths are generated by a reflex response similar to the human Hoffmann (H)-reflex which is assigned to a monosynaptic excitation of spinal $\alpha$-motor neurons, preferably by primary muscle spindle afferents. With rising stimulus strengths, this H-reflex is preceded by a second EMG wave of shorter latency, the so-called M-wave, which is attributable to direct stimulation of the axons of the alpha motor neurons. Ten consecutive reflex responses were meaned by a computer program both before (control) and also after intraperitoneal or after intrathecal injection of the solvent or of the various substances. The size of the M-wave and of the H-reflex was determined by measuring the peak-to-peak amplitude.

To trigger the flexor reflex, one rear paw was stimulated using a pair of fine, subcutaneous needle electrodes (5 consecutive square impulses with a stimulus frequency of 500 Hz, of in each case 0.2 ms duration and a stimulus intensity three times that of the reflex threshold). EMG leads were recorded with a pair of fine needle electrodes from the ipsilateral N. tibialis. Seven consecutive EMG responses were rectified and meaned using a PC both before and after intraperitoneal or intrathecal injection of the solvent or substances. The size of the flexor reflex was derived from the area between the reflex curves and the base line.

In all reflex investigations the measured values were given after injection of solvents or substances in percent of the appropriate control value before the injection. The statistical analysis was carried out using the Mann-Whitney U-test.

The rats were fitted with polyethylene catheters (PE10) for the intrathecal injection. The Membrana atlanto-occipitalis was exposed and carefully slit in the area of the median line. The catheter was then introduced into the spinal canal and the tip pushed forward into the region of the lumbar marrow. The injection of solvents or substances occurred in a volume of 5 ul at an infusion rate of 1 ul per minute. 10 ul solvent was then subsequently injected to ensure that the entire amount of substance passed through the catheter into the spinal canal.

When the experiments had been completed, the exact localisation of the catheter tip was confirmed by injecting 2% Evans Blue ink through the catheter.

Flupirtine (ASTA Medica AG, Germany), yohimbine hydrochloride (Sigma Chemicals, U.S.A.) and prazosin (RBI, U.S.A.) were dissolved in physiological salt solution. NMDA (Sigma), bicuculline methiodide (Sigma), 6,7-dinitroquinoxaline-2,3-dione (DNQX) (RBI, U.S.A.) and ATPA (kindly provided by Dr. Turski, Schering, Germany) were dissolved in a small amount of 1 Mol NaOH and the volume made up with salt solution. Phaclofen (Tocris, Great Britain) was dissolved in 0.2N HCl and the final volume also made up with salt solution.

Flumazenil (kindly provided by Prof. Haefely, Hoffmann-La Roche, Switzerland) was dissolved in Tween 80 and distilled water. The pH value of all solutions was adjusted to 7.2–7.4. Neither the monosynaptic H-reflex nor the polysynaptic flexor reflex were influenced during the intraperitoneal injection of the solvent, the systemic administration of flupirtine in doses of 1 to 10 mg per kg body weight reducing the flexor reflex in dose-dependent manner (FIG. 1 to FIG. 3). The effect of flupirtine occurred within 10 minutes, reached its maximum 10 to 30 minutes after the injection and lasted about 20 to 60 minutes, depending on the dose.

In contradistinction hereto, the H-reflex was unaffected by flupirtine. Even the highest dose of flupirtine (10 mg per kg), which reduced the flexor reflex to about 50% of the initial value, had no effect on the H-reflex (FIG. 3).

The different effect of the flupirtine on the flexor reflex and H-reflex was also confirmed after intrathecal administration. In doses of 33–330 nmol, flupirtine reduced the flexor reflex after intrathecal administration without changing the H-reflex (FIG. 4). This effect also appeared within 10 minutes and lasted 40–60 minutes, depending on the dosage selected (FIG. 5). Intrathecal injection of the solvent influenced neither the flexor reflex nor the H-reflex. The M wave was neither changed by the administration of solvent nor by the injection of flupirtine. This proves the stability of the preparation selected. The animal pharmacological data were confirmed in the context of human pharmacological reflex investigations. In man, too, (p.o. administration), flupirtine only lowers the flexor reflex whereas the H-reflex remains unaffected.

To obtain insight into whether changes in the transmission of GABA, noradrenalin or excitatory amino acids are involved in the muscle-relaxant effect of flupirtine, we investigated the influence of various substances, which attack these receptors as agonists or antagonists, on the muscle-relaxant effect of flupirtine. The depressor effect after intrathecal administration of flupirtine (165 nmol) on the flexor reflex was not influenced by the co-administration of the $GABA_A$-antagonist bicuculline (1 nmol) and of the $GABA_B$-antagonist Phaclofen (100 nmol) (FIG. 6) of the $\alpha_1$-antagonist prazosin (10 nmol) (FIG. 7) or the excitatory amino acid ATPA (α-amino-3-hydroxy-5-terthyl-4-isoxazoleproprionic acid) (0.1 pm ) (FIG. 8), which constitutes a potent agonist at the quisqualate receptor. The effect of flupirtine was also uninfluenced by the intraperitoneal injection of the benzodiazepine antagonist flumazenil (5 mg/kg). The flumazenil had to be given systemically because it could not be applied intrathecally because of its insolubility in water. In contrast thereto, the co-administration of the mixed $\alpha_1$-$\alpha_2$-antagonist yohimbine (10 nmol) (FIG. 7) or of the excitatory amino acid NMDA (0.1 nmol) (FIG. 8) prevented the effect of flupirtine on the flexor reflex. Bicuculline, phaclofen, prazosin, ATPA, flumazenil, yohimbine and NMDA were given in doses which, in themselves, do not influence the size of the reflex (FIG. 6–9), but which suffice to in each case antagonise the depressor effect of the $GABA_A$-agonist muscimol, of the α-agonist tizanidine and of the NMDA-antagonist 2-amino-phosphonoheptanoate (AP7) and memantine (Schwarz et al., 1992) on spinal reflexes.

The experiments consequently show that the polysynaptic flexor reflexes are reduced in dose-dependent manner both after intraperitoneal (1–10 mg/kg body weight) and after intrathecal (33–330 n Mol) administration of flupirtine without impairing the monosynaptic Hoffmann (H)-reflex.

In these experiments, the co-administration of the excitatory amino acid N-methyl-D-aspartate (NMDA) reduces the muscle-relaxant effect of flupirtine. In accordance with these findings, the effect of flupirtine is, inter alia, mediated via inhibition of the transmission of excitatory amino acids. In this case, the transmission mediated via NMDA receptors is particularly impaired.

DESCRIPTION OF THE DRAWINGS

FIGS. 1(a–d): Flexor reflex (upper tracing) of the M. tibialis, triggered by electrical stimulation (5 stimuli, frequency 500 Hz, three times the reflex threshold) of the rear paw and Hoffmann (H)-reflex and M-wave (lower tracing) derived from the plantar foot muscles after electric stimulation (single stimulus, twice the reflex threshold) of the N. tibialis (pre-drug) and 20 minutes after (flupirtine) intraperitoneal injection of flupirtine, 10 mg/kg. Stimulus artefacts are marked with arrows.

FIG. 2: Time course of the effect after intraperitoneal injection of solvent or various doses of flupirtine on the size of the flexor reflex. Abscissa: time in minutes after the injection, ordinate: size of the flexor reflex in percent of the corresponding value before the injection (mean values±SEM of in each case 6–8 animals). Significances p<0.01, *p<0.001 vs. solvent (Mann-Whitney U-test)

FIGS. (a and b): Effect of the intrathecal injection of flupirtine (33–330 nmol) on the size of the flexor reflex (top) and of the H-reflex (bottom). The size is expressed as a percentage of the appropriate value before the injection (mean value±SEM of in each case 7–10 animals). C: solvent, doses in nmol, significances p<0.01, *p<0.001 vs. solvent (Mann-Whitney U-test).

FIG. 5: Time course of the effect after intrathecal injection of solvent or various doses of flupirtine (33–330 nmol) on the size of the flexor reflex. Abscissa: time in minutes after the injection, ordinate: size of the flexor reflex in percent of the corresponding value before the injection (mean values±SEM of in each case 7–10 animals). Significances *p<0.05, p 0.01, *p<0.001 vs. solvent (Mann-Whitney U-test).

Figure 3A:
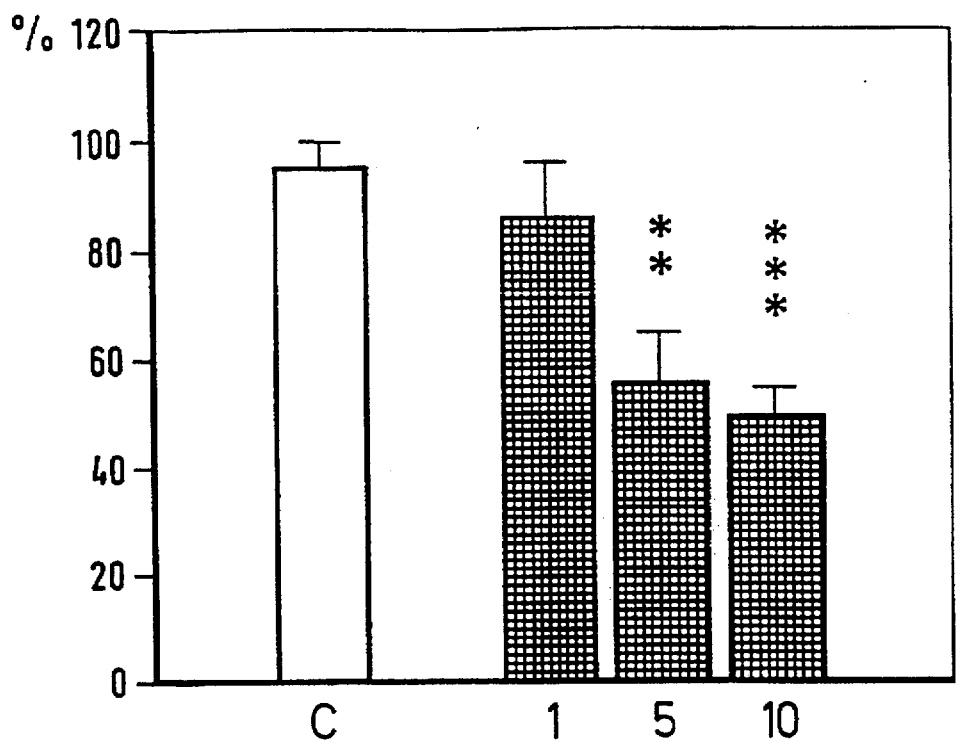
FIGS. 3(a and b): Effect of the intraperitoneal injection of flupirtine (1–10 mg/kg) on the size of the flexor reflex (top) and of the H-reflex (bottom). The size is expressed as a percentage of the appropriate value before the injection (mean value±SEM of in each case 6–8 animals). C: solvent, significances p<0.01, *p<0.001 vs. solvent (Mann-Whitney U-test)
Figure 3B:
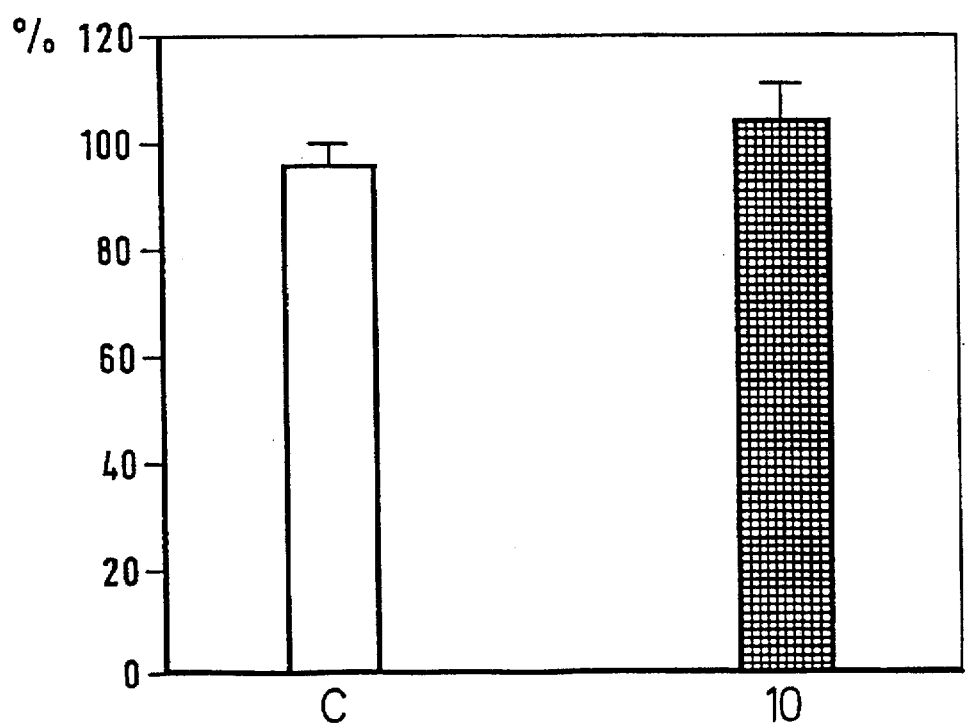
Figure 4A:
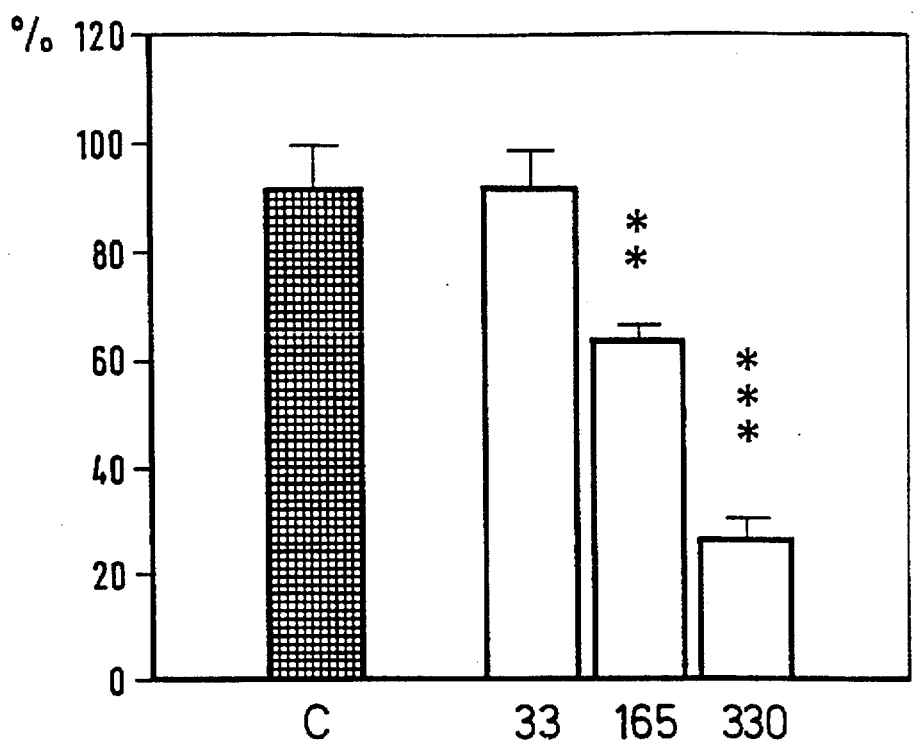
Figure 4B:
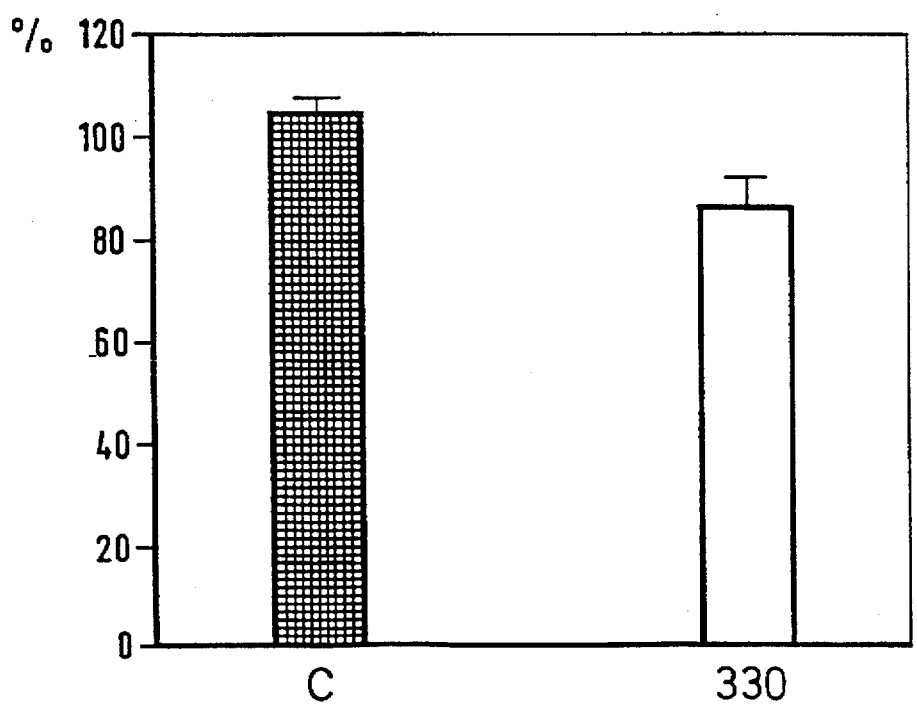
Figure 6A:
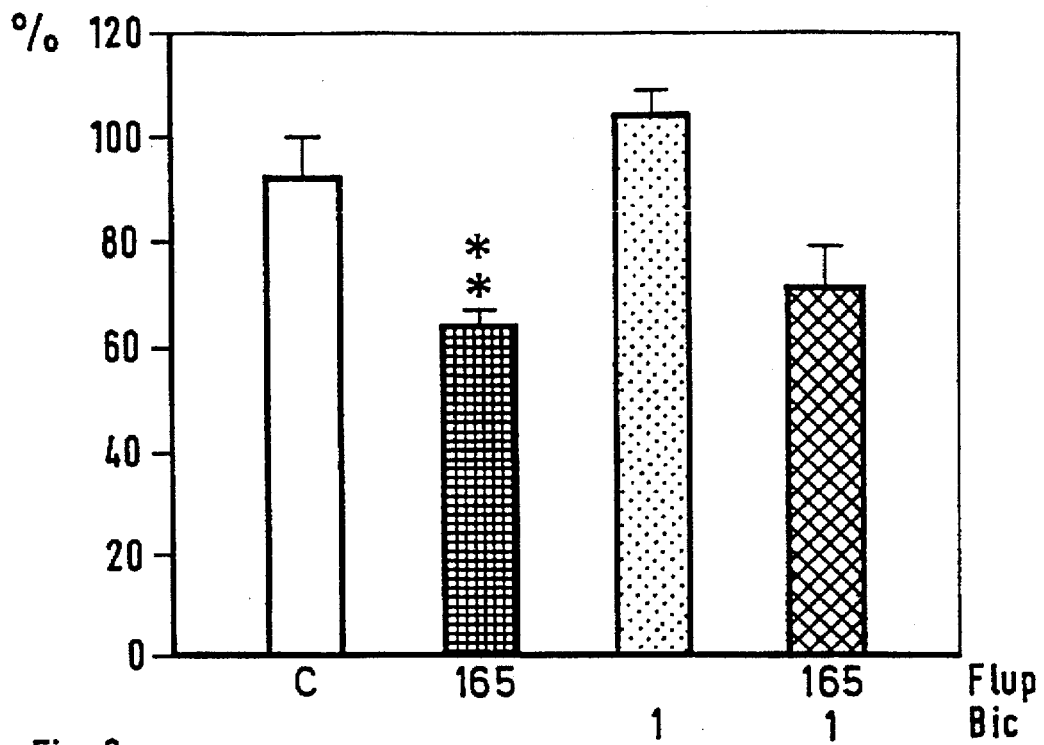
Figure 6B:
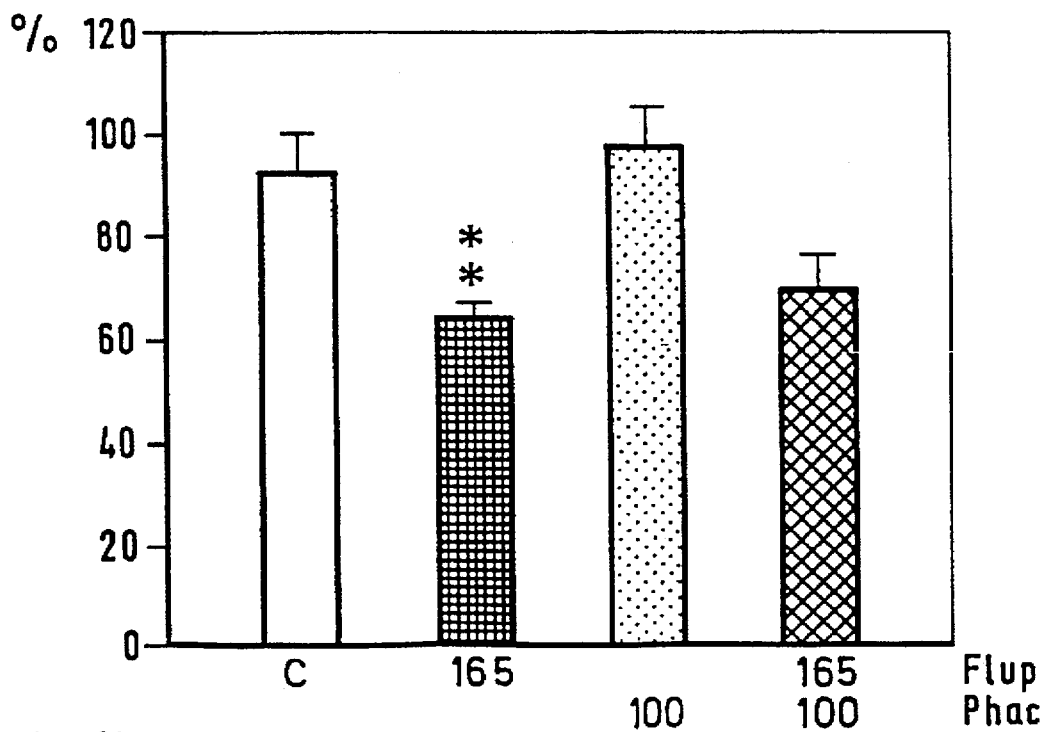

FIGS. 6(a and b): Effect of the intrathecal injection of bicuculline (Bic; top) or phaclofen (Phac; bottom) and flupirtine on the size of the flexor reflex, doses in nmol, significances p<0.01, *p<0.001 vs. solvent (Mann-Whitney U-test)

Figure 7A:
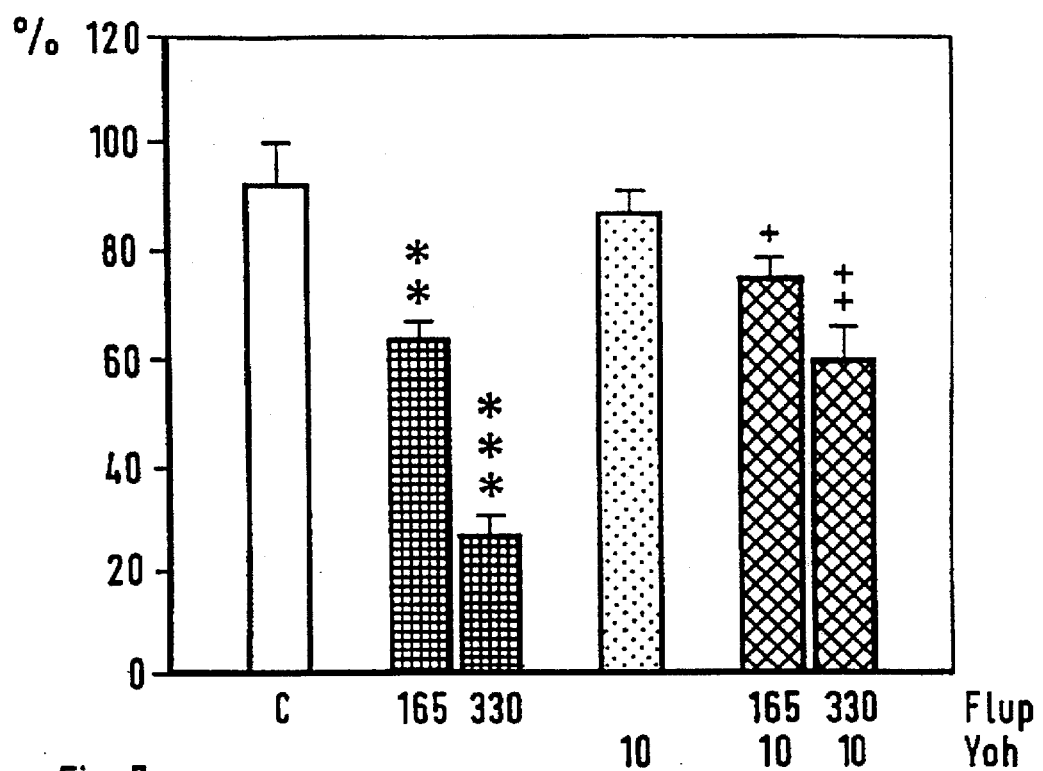
Figure 7B:
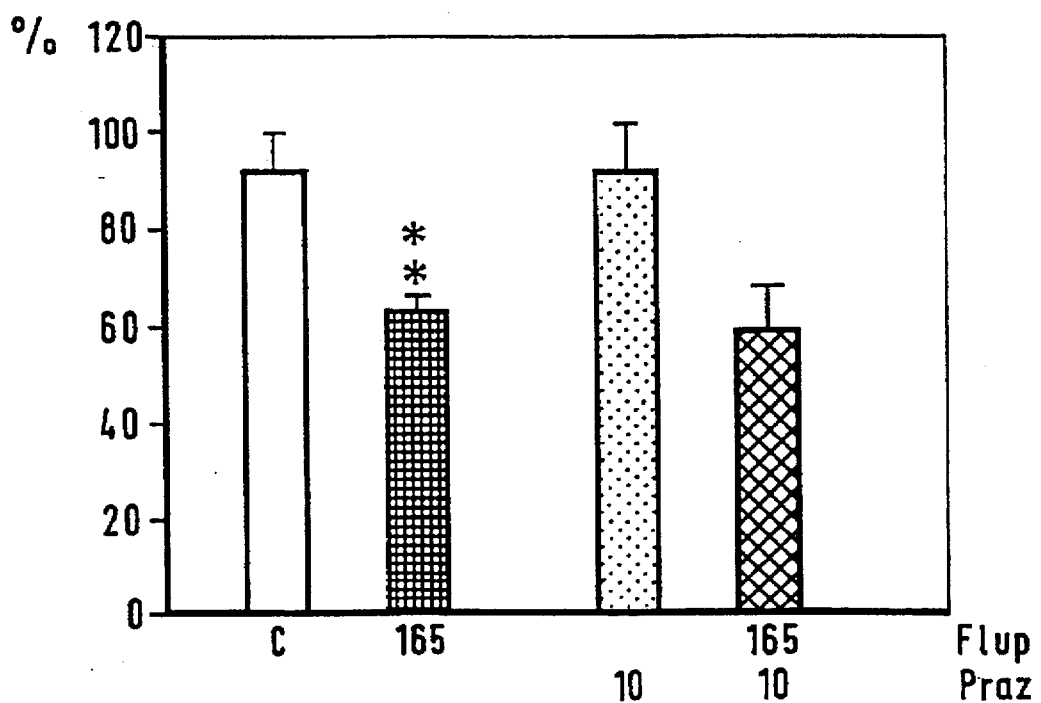

FIGS. 7(a and b): Effect of the intrathecal injection of yohimbine (Yoh; top) or prazosin (Praz; bottom) and flupirtine on the size of the flexor reflex, doses in nmol, significances p<0.01, *p<0.001 vs. solvent; p<0.05, ++p<0.01 vs. flupirtine (Mann-Whitney U-test)

Figure 8A:
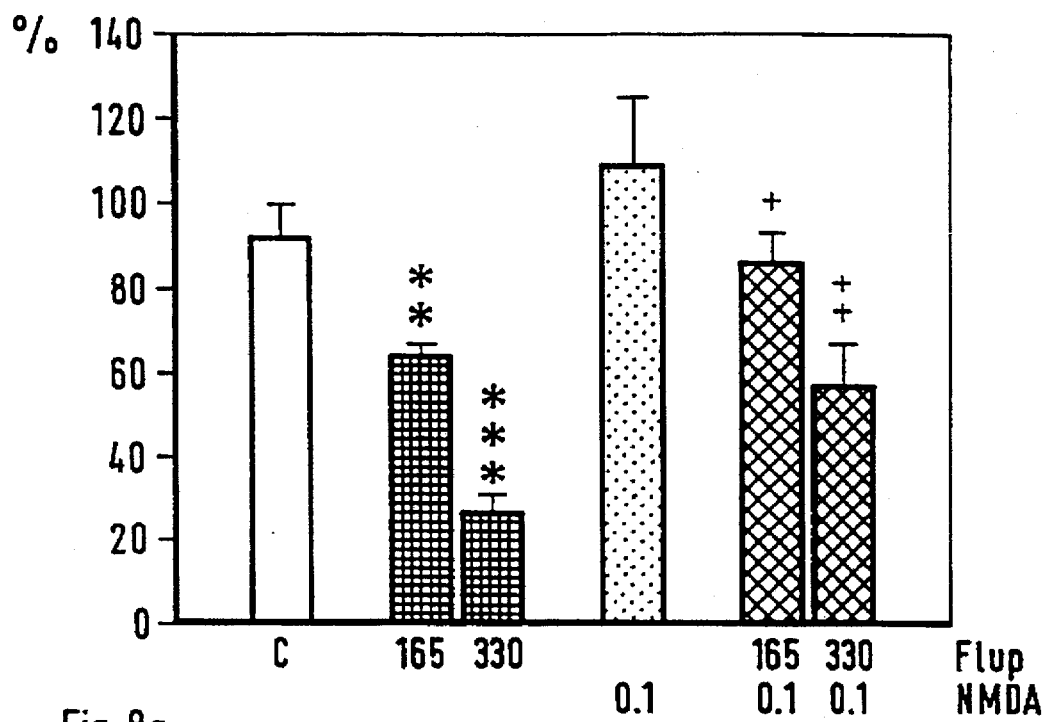
Figure 8B:
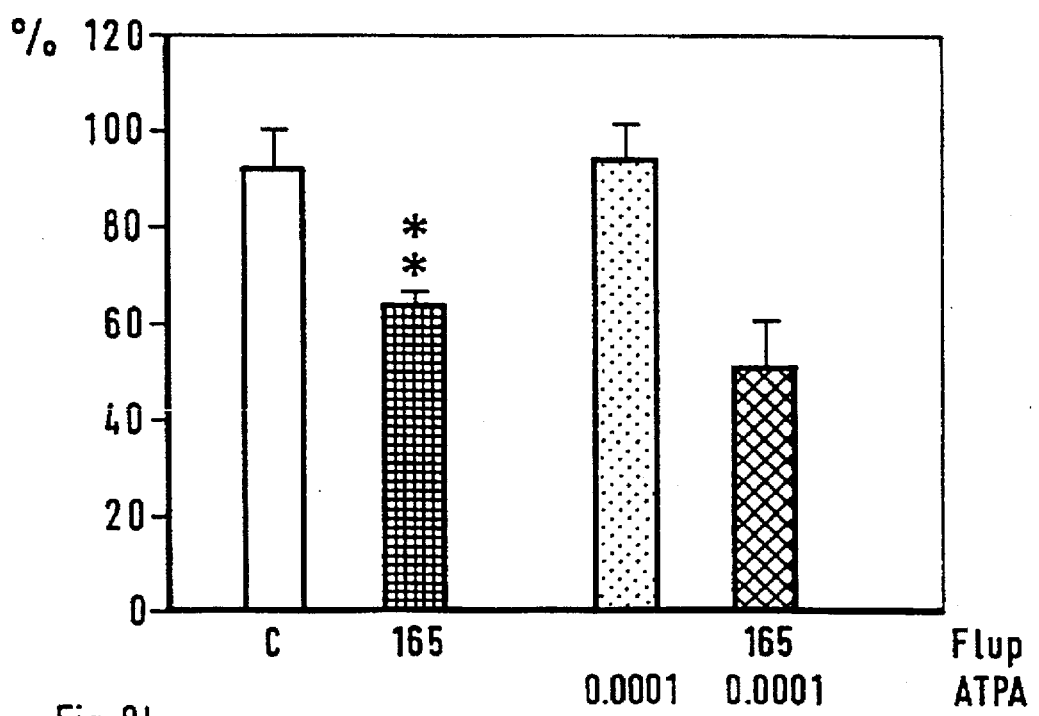

FIGS. 8(a and b) : Effect of the intrathecal injection of NMDA (top) or ATPA (bottom) and flupirtine on the size of the flexor reflex, doses in nmol, significances p<0.01, *p<0.001 vs. solvent; +p<0.05, +++p<0.01 vs. flupirtine (Mann-Whitney U-test)

Figure 9:
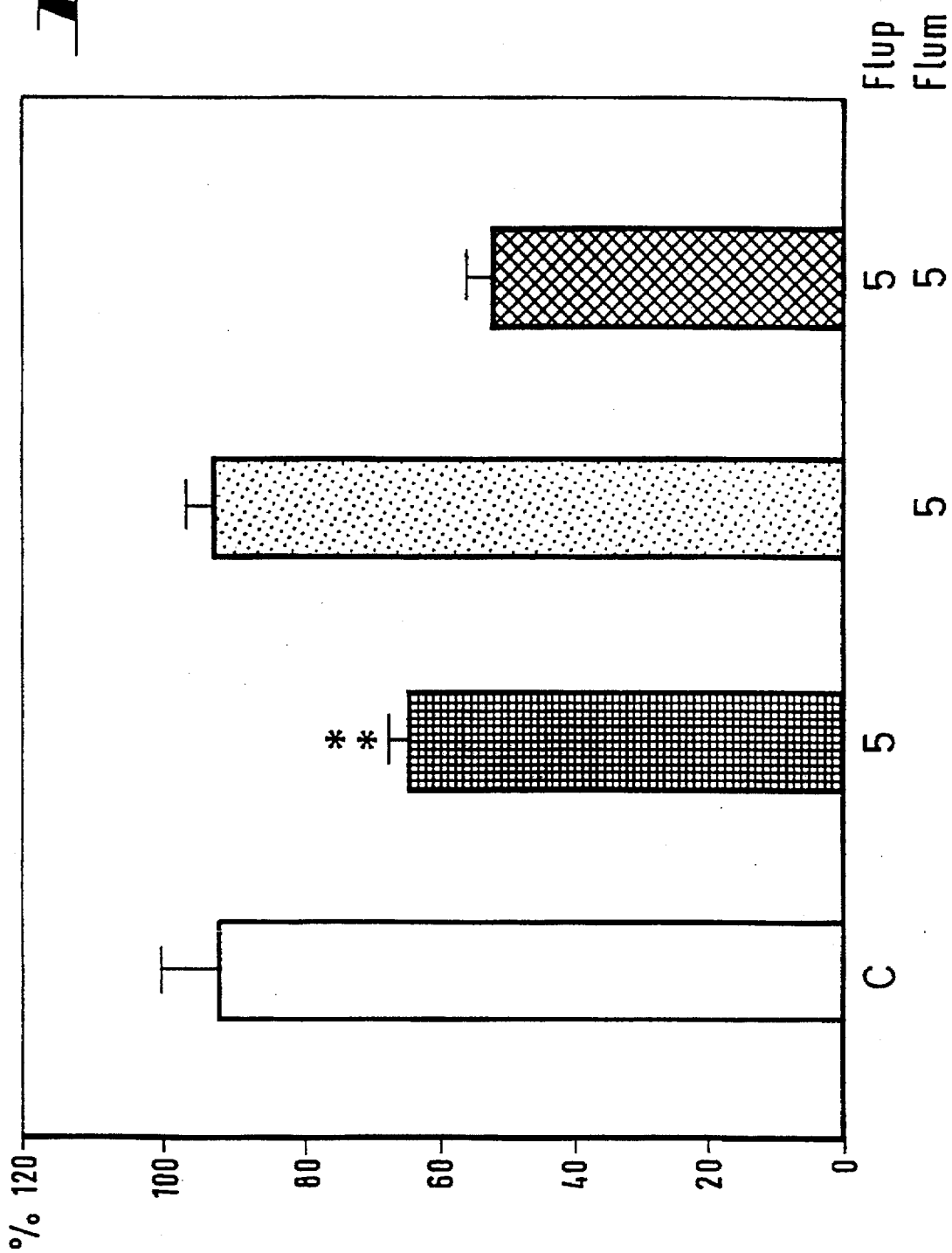

FIG. 9: Effect of the intraperitoneal injection of flumazenil (Flum) and the intrathecal injection of flupirtine on the size of the flexor reflex. Doses. in mg/kg (Flum) and nmol (Flup). Significances p<0.01, *p <0. 001 (Mann-Whitney U-test).

It is an object of the invention to provide medicinal formulations containing the active substance flupirtine for use in neurodegenerative disorders and similar disorders.

Disorders that may be treated on the basis of the pharmacological results with flupirtine are for example cerebral ischaemia, idiopathic Morbus Parkinson, topically- or drug-induced Parkinson syndrome, Morbus Alzheimer and cerebral dementia syndromes of different origin, Huntington's chorea; multiple sclerosis, amyotrophic lateral sclerosis, infectious-induced neurodegeneration disorders such as AIDS-encephalopathy, Creutzfeld-Jakob disease, encephalopathies induced by rubiola and herpes viruses and borrelioses, metabolic-toxic neurodegenerative disorders such as hepatic-, alcoholic-, hypoxic-, hypo- or hyperglycemically-induced encephalopathies as well as encephalopathies induced by solvents or pharmaceuticals, degenerative retina disorders of various origin, traumatically-induced brain and bone marrow damage, cerebral hyperexcitability symptoms of varying origin such as after the addition of and/or withdrawal of medicaments, toxins, noxae and drugs, mentally and traumatically-induced cerebral hyperexcitability states, neurodegenerative syndromes of the peripheral nervous system, such as metabolism, medicament, toxically- and infectiously-induced polyneuropathies and polyneuritis, the bronchospasmolytic effect can also be utilised.

It is also possible to use flupirtine with anti-Parkinson agents such as L-dopa and various dopamine agonists separately, in succession, or in the form of a combination medicament. The dosage of the invention when used as combination medicament in the use of L-dopa as a combination partner is 2 mg–200 mg L-dopa[1] and 5 mg–100 mg flupirtine, when dopamine agonists are used, such as bromocriptine as combination partner 0.5mg–10 mg bromocriptine and 5 mg–100 mg flupirtine, when lisuride is used as combination partner 0.05 mg–0.2 mg lisuride and 5 mg–100 mg flupirtine, when pergolide is used as combination partner 0.01 mg–1 mg pergolide and 5 mg–100 mg flupirtine, when the MAO-B inhibitor selegilin is used 0.1 mg–5 mg selegilin and 5 mg–100 mg flupirtine.

[1] as fixed combination with benserazide or carbidopa

Similarly, flupirtine may be administered separately with antioxidants, anti-epileptics, circulation-promoting medicaments and neuroleptics or given as a combination medicament.

The properties of flupirtine also permit use in neuroleptic analgesia, alone or with other neuroleptics. Dosage forms that may for example be considered are: tablets, film-coated tablets, hard gelatin capsules, soft gelatin capsules, pellets, granulates, coated tablets, suppositories, microcapsules, aqueous or oily suspensions, oily solutions, injection solutions for intramuscular and intrathecal administration, injection solutions and infusion solutions for intravenous administration. Suitable salts for the preparation of the medicament are all physiologically acceptable salts of flupirtine. It is, for example, possible to use the chloride, the maleate, the sulfate and the gluconate of flupirtine. The following dosage information always relates to flupirtine as a base. If salts of flupirtine are used, a conversion should be made according to the molecular weight.

It is also possible to convert flupirtine into a sustained release form using the methods described in German published specification 39 12 292.

The amounts of flupirtine in the medicaments of the invention are 10 mg–3000 mg, preferably 20 mg–2000 mg and particularly preferred 50 mg–1500 mg. The cited individual doses of the medicament may be administered orally, rectally, intravenously, intrathecally or intramuscularly, 1–5 times, preferably 1–3 times, in particular 1–2 times daily.

What is claimed is:

1. A method of treating cerebral ischemia comprising administering an effective amount of flupirtine to an individual in need of such treatment.

2. A method of treating a neurodegenerative disease or disorder other than Parkinson's Disease comprising administering an effective amount of flupirtine to an individual in need of such treatment.

3. The method of claim 2 which additionally comprises administration of a dopamine antagonist.

4. The method of claim 2 which additionally comprises administration of L-dopa.

5. The method of claim 4 which additionally comprises administration of a dopamine antagonist.

6. The method of claim 2 wherein said disease or disorder is Alzheimer's Disease.

7. The method of claim 2 wherein said disease or disorder is Huntington's Chorea.

8. The method of claim 2 wherein said disease or disorder is multiple sclerosis.

9. The method of claim 2 wherein said disease or disorder is an infection-induced neurodegenerative disorder.

10. The method of claim 2 wherein said disease or disorder is a metabolic-toxic neurodegenerative disorder.

11. A method of treating a degenerative or ischemic disorder of the retina comprising administering an effective amount of flupirtine to an individual in need of such treatment.

12. A method of treating trauma induced brain or bone marrow damage comprising administering an effective amount of flupirtine to an individual in need of such treatment.

13. A method of treating a cerebral hyperexcitability syndrome comprising administering an effective amount of flupirtine to an individual in need of such treatment.

14. A method of treating a neurodegenerative syndrome of the peripheral nervous system comprising administering an effective amount of flupirtine to an individual in need of such treatment.

15. A method of inducing neuroleptic analgesia comprising administering an effective amount of flupirtine to an individual in need of such analgesia.

* * * * *